United States Patent [19]
Yamauchi et al.

[11] Patent Number: 5,479,462
[45] Date of Patent: Dec. 26, 1995

[54] METHOD FOR PRODUCING METHANOL BY USE OF NUCLEAR HEAT AND POWER GENERATING PLANT

[75] Inventors: Yasuhiro Yamauchi; Yuuji Tokita; Nobuaki Murakami; Katsuhiko Takita; Yasushi Mori; Kensuki Muraishi; Shozo Kaneko; Satoshi Uchida, all of Nagasaki; Nobuhiro Ukeguchi, Tokyo; Seiichi Shirakawa, Nagasaki, all of Japan

[73] Assignee: Mitsubishi Jukogyo Kabushiki Kaisha, Tokyo, Japan

[21] Appl. No.: 209,921

[22] Filed: Nov. 3, 1993

Related U.S. Application Data

[62] Division of Ser. No. 827,770, Jan. 29, 1992, Pat. No. 5,312,843.

[30] Foreign Application Priority Data

Jan. 29, 1991 [JP] Japan ............................... 3-9174
Jan. 31, 1991 [JP] Japan ............................... 3-10653
Feb. 14, 1991 [JP] Japan ............................... 3-20929

[51] Int. Cl.$^6$ ............................................ G21D 9/00
[52] U.S. Cl. ............................................ 376/325; 376/317
[58] Field of Search ........................ 376/317, 323–325; 204/129; 518/702–704

[56] References Cited

U.S. PATENT DOCUMENTS

| | | | |
|---|---|---|---|
| 3,993,653 | 11/1976 | Blum et al. | 204/129 |
| 4,021,299 | 5/1977 | Rigollot | 376/325 |
| 4,084,038 | 4/1978 | Scragg et al. | 429/19 |
| 4,087,976 | 5/1978 | Morrow, Jr. et al. | 60/643 |
| 4,092,129 | 5/1978 | Goudal | 204/129 |
| 4,158,637 | 6/1979 | Jones | 376/325 |
| 4,274,938 | 6/1981 | Schulten et al. | 204/239 |
| 4,337,067 | 6/1982 | Jager | 376/325 |
| 4,339,547 | 7/1982 | Corbett et al. | |
| 4,428,905 | 1/1984 | Phillips et al. | 376/323 |
| 4,568,522 | 2/1986 | Corbett | 422/186 |
| 4,728,584 | 3/1988 | Isenberg | 429/31 |

FOREIGN PATENT DOCUMENTS

| | | |
|---|---|---|
| 2927641 | 1/1981 | Germany . |
| 2086389 | 5/1982 | United Kingdom . |

*Primary Examiner*—Behrend E. Harvey
*Attorney, Agent, or Firm*—Wenderoth, Lind & Ponack

[57] ABSTRACT

Provided herein is a process for producing methanol which was developed to reduce the emission of carbon dioxide which is responsible for global warming. The process involves the steps of generating steam by the use of nuclear heat of a high-temperature gas-cooled nuclear reactor, decomposing the steam into hydrogen by means of a steam electrolyzer, and synthesizing methanol from this hydrogen and carbon dioxide obtained from a carbon dioxide source. The process also involves the steps of converting carbon dioxide and hydrogen into carbon monoxide and steam by means of a reverse shift reactor, forming hydrogen and carbon monoxide of almost the same composition as the conventional one, and reacting said hydrogen and carbon monoxide into methanol by means of a methanol synthesis column. The process permits the use of an existing methanol production facility. The process may be modified such that the gasified gas composed of carbon monoxide, carbon dioxide, and hydrogen is mixed with hydrogen gas generated by the steam electrolyzer, and the resulting mixed gas is converted into methanol. Also, a power generating plant is provided in which oxygen enriched air, generated by the steam electrolyzer using nuclear heat of the high-temperature gas-cooled nuclear reactor, is used as combustion air.

10 Claims, 5 Drawing Sheets

METHOD FOR PRODUCING METHANOL BY USE OF NUCLEAR HEAT AND POWER GENERATING PLANT

This is a Divisional application of Ser. No. 07/827,770, filed Jan. 29, 1992, now U.S. Pat. No. 5,312,843.

BACKGROUND OF THE INVENTION

1. Field of the Invention

The present invention relates to a process for producing methanol by the use of high-temperature nuclear heat generated by a high-temperature gas-cooled nuclear reactor (HTGR for short hereinafter), and a power generating plant using high-temperature nuclear heat generated by an HTGR.

2. Description of the Prior Art

Reducing the amount of carbon dioxide ($CO_2$) emitted by the plants of various industries is a key to solving the problem associated with global warming. Automobiles are responsible for about 20% of the total amount of carbon dioxide emitted in Japan. Therefore, it is important to reduce the amount of carbon dioxide in automotive exhaust gas. As a means to cope with this situation, methanol has attracted public attention. Methanol is a promising substitute for gasoline because it gives rise to less carbon dioxide per calorific value and a very small amount of nitrogen oxides ($NO_x$). Methanol is conventionally produced from natural gas through its decomposition into hydrogen and carbon monoxide (CO) with the steam reforming reaction and their synthesis into methanol with the aid of a copper catalyst.

The conventional process comprises, as FIG. 5 shows, the steps of decomposing natural gas or naphtha (as the feedstock) into hydrogen ($H_2$), carbon monoxide (CO), and carbon dioxide ($CO_2$) by a steam reforming reaction carried out in a reformer 01, compressing these gases with a compressor 02, supplying them to a methanol synthesis tower 03, in which the reaction of CO and $H_2$ takes place to obtain crude methanol with the aid of a copper catalyst, separating the crude methanol with a high-pressure separator 04, and refining the crude methanol in a distillation column 05.

Synthetic methanol produced by the conventional process as mentioned above does not contribute to the reduction of carbon dioxide emitted by the industry, because when such methanol is combusted it gives rise to the same amount of carbon dioxide as natural gas, so long as it is produced from natural gas.

The present invention was developed with the foregoing in mind to provide a new process for producing methanol which meets recent environmental requirements.

SUMMARY OF THE INVENTION

It is an object of the present invention to provide a process for producing methanol by the use of nuclear heat, said process comprising generating hydrogen, by means of a steam electrolyzer containing a solid electrolyte, from steam generated by nuclear heat of an HTGR, and synthesizing methanol from said hydrogen and carbon dioxide obtained from a carbon dioxide source such as thermoelectric power station.

The above-mentioned process for producing methanol further comprises decomposing carbon dioxide and hydrogen into carbon monoxide and steam by means of a reverse shift reactor and synthesizing methanol in a methanol reactor from the carbon monoxide and the hydrogen discharged from the steam electrolyzer.

Also, it is an object of the present invention to provide a power generating plant which can effectively make use of the high temperature nuclear heat generated by an HTGR.

The above-mentioned first or second process for producing methanol further comprises performing electrolysis in the steam electrolyzer containing a solid electrolyte by the use of electric power generated by nuclear heat of the HTGR.

The process of the present invention also comprises generating hydrogen from steam in a steam electrolyzer containing a solid electrolyte by the use of high-temperature nuclear heat of an HTGR, adding said hydrogen to a gasified gas composed of carbon monoxide, carbon dioxide, and hydrogen, the gas having been produced by the gasification of a fossil fuel (such as natural gas, petroleum, or coal), thereby producing a gaseous mixture, decomposing carbon dioxide and hydrogen of the gaseous mixture into carbon monoxide and steam by a reverse shift reaction, and using the resulting gas for the synthesis of methanol.

The above-mentioned process is characterized in that electrolysis in the steam electrolyzer containing a solid electrolyte is performed by the use of electric power generated by nuclear heat of an HTGR.

The above-mentioned process is further characterized in that the oxygen generated by the steam electrolyzer is used as an oxidizing agent for the production of the gasified gas.

The power generating plant according to the present invention comprises an apparatus for producing hydrogen in a steam electrolyzer cell by using high temperature nuclear heat generated by an HTGR, and a power generating apparatus supplied with oxygen enriched air generated in said steam electrolyzer cell.

According to a first aspect of the present invention, methanol is synthesized from carbon dioxide emitted from thermoelectric power stations and hydrogen produced by means of the steam electrolyzer containing a solid electrolyte by the use of nuclear heat of the HTGR. The resulting methanol does not add to the carbon dioxide in the atmosphere after it is used as an automotive fuel. This contributes to the reduction of the emission of carbon dioxide which is a pressing problem in the industry. Methanol offers an additional advantage of giving rise to a less amount of carbon dioxide per calorific power on account of the added hydrogen.

According to a second aspect of the present invention, carbon monoxide and hydrogen as the raw materials of methanol are produced with a reverse shift reactor. This offers an advantage in that the feedstock has almost the same composition as that used in the conventional process. This, in turn, makes it possible to use the existing production facility and technology for methanol synthesis.

According to a third aspect of the present invention, electric power generated by the nuclear heat of HTGR is effectively used for performing electrolysis in the steam electrolyzer containing a solid electrolyte.

According to a fourth aspect of the present invention, the steam electrolyzer containing a solid electrolyte produces hydrogen from steam by the aid of high-temperature nuclear heat of the HTGR and electric power generated by the nuclear heat. This hydrogen may be regarded as a converted form of nuclear energy. Therefore, it may be said that the methanol synthesized from this hydrogen and a gas composed of carbon monoxide, carbon dioxide, and hydrogen has nuclear energy in a converted form. The thus synthesized methanol, on combustion, gives rise to the same amount of carbon dioxide as the fossil fuel from which it is derived; but it gives rise to a less amount of carbon dioxide per calorific power on account of the added hydrogen. In addition, the process of the present invention employs the reverse shift reaction to decompose carbon dioxide and hydrogen into carbon monoxide and steam. This offers an advantage in that the feedstock gas has the same composition as that for the conventional process. Therefore, this makes it possible to use the existing production facility and technology for methanol synthesis. The process of the present invention employs the steam electrolyzer which generates oxygen as well as hydrogen. This oxygen can be used as an oxidizing agent for the gasification of the fuel.

According to a fifth aspect of the present invention, electric power generated by the nuclear heat of the HTGR is effectively used for performing electrolysis in the steam electrolyzer containing a solid electrolyte.

According to a sixth aspect of the present invention, the oxygen generated by steam electrolysis in the steam electrolyzer is effectively used as an oxidizing agent for the production of gasified gas.

According to a seventh aspect of the present invention, by utilizing the oxygen-enriched air generated in the steam electrolyzer cell, the power necessary for producing the oxygen-enriched air is reduced compared to that for producing the oxygen-enriched air from air using a nitrogen separator such as pressure-swing type of separator. Accordingly, it is possible to reduce the total power consumed in the plant.

DETAILED DESCRIPTION OF THE PREFERRED EMBODIMENTS

First Embodiment

Figure 1:
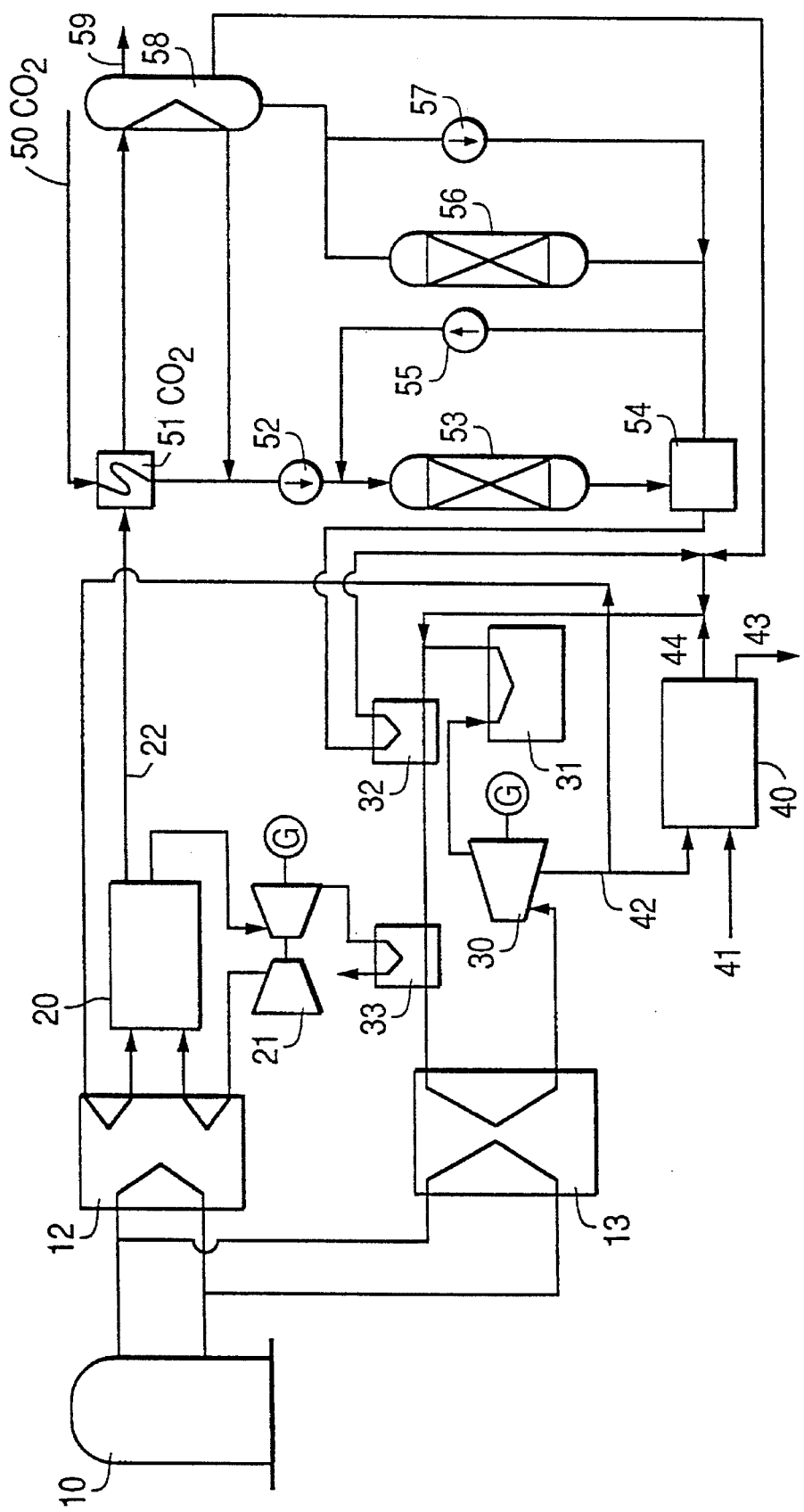
FIG. 1 is a schematic diagram of the first embodiment of a power generating plant according to the present invention.

The first embodiment of the present invention will be described with reference to FIGS. 1 and 2. Referring to FIG. 1, an HTGR 10 discharges high-temperature helium gas. The helium gas enters the intermediate heat exchanger 12 and steam generator 13 to supply them with heat. The steam generator 13 generates steam which enters the steam turbine 30 to drive it. The steam turbine 30 generates electric power necessary for electrolysis explained below. The steam turbine 30 discharges steam which passes through the condenser 31 and the feed water heaters 32 and 33 and returns to the steam generator 13.

The steam turbine 30 has a low-pressure stage which permits steam (at 10 atm) to bleed. Part of the bleeding steam 42 enters the high-temperature steam electrolyzer 20 explained below and the remainder enters the seawater desalination unit 40, which is supplied with seawater 41 and discharges fresh water 44 and concentrated seawater 43. The fresh water 44 is fed to the power plant after mixing with the condensed water discharged from the condenser 31.

The high-temperature steam electrolyzer 20 is supplied with part of the bleeding steam 42 from the low-pressure stage of the steam turbine 30 after it has been heated to 700°–1000° C. by the intermediate heat exchanger 12. The high-temperature steam electrolyzer 20 is also supplied with air for heating and heat removal which is compressed to about 10 atm by the compressor coupled to the gas turbine 21 (explained later). The air is heated to 700°–1000° C. by the intermediate heat exchanger 12.

Figure 2:
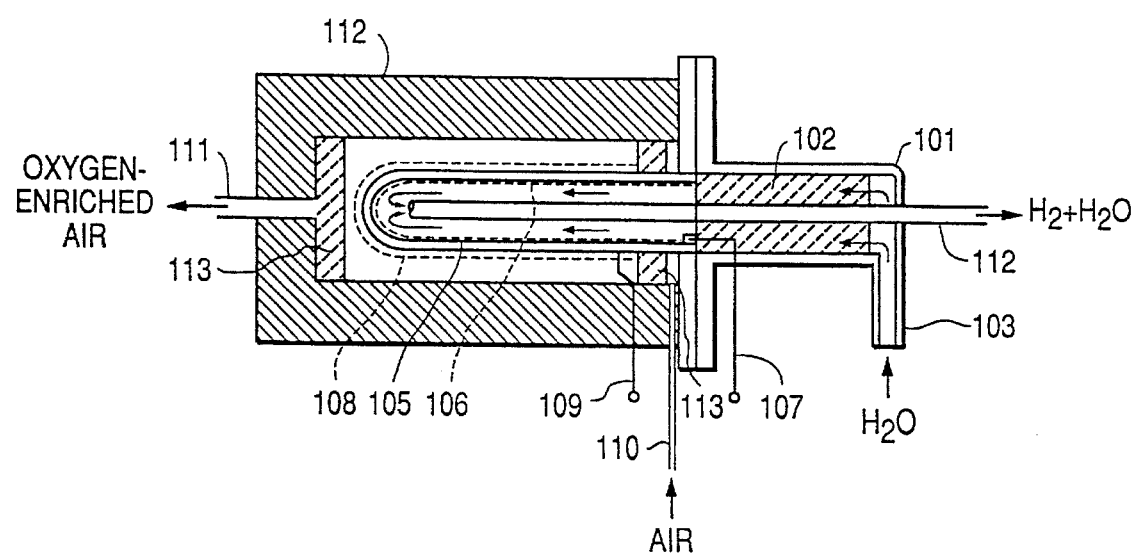
FIG. 2 is a sectional view of the high-temperature steam electrolyzer used in the first embodiment of the present invention.

The high-temperature steam electrolyzer 20 as shown in FIG. 2 is provided with a known electrolytic cell containing a solid electrolyte. It is disclosed in, for example, Japanese Patent Application No. 271288/1989. The electrolyzer has a porous ceramic part 102 enclosed in a quartz glass container 101. The porous ceramic part 102 is supplied with steam from the steam inlet 103. (This steam is part of the steam 42 bled from the low-pressure stage of the steam turbine 30 and is heated to 1000° C. by the intermediate heat exchanger 12.) The high-temperature steam enters the cylindrical electrolytic cell 105 made of yttrium-stabilized zirconia (YSZ for short hereinafter) and the like as a solid electrolyte. The electrolytic cell 105 has a hydrogen electrode 106 made of platinum- or nickel-YSZ cermet and an oxygen electrode 108 made of perovskite-type oxide of platinum or lanthanum ($LaCoO_3$, $LaMnO_3$, $LaCrO_3$, etc.). The former is connected to a cathode 107 and the latter to an anode 109. Upon application of direct current, the steam is electrolyzed, and the hydrogen electrode 106 generates hydrogen gas and the oxygen electrode 108 generates oxygen gas. The oxygen gas is discharged (in the form of oxygen-enriched air) from the outlet 111 of the electrolytic cell with the hot air which has been compressed by the compressor coupled to the gas turbine 21, has been heated to 1000° C. by the intermediate heat exchanger 12 and has been admitted through the air inlet 110.

The electrolytic cell 105 is covered with a heat insulator 112 to keep the temperature inside the cell constant and to prevent heat dissipation. The air inlet 110 and outlet 111 may be provided with a porous ceramic part 113 for uniform temperature distribution. The hydrogen gas is discharged from the hydrogen outlet 112.

As mentioned above, the high-temperature steam electrolyzer 20 decomposes steam into hydrogen gas and oxygen gas. It discharges the oxygen gas in the form of oxygen-enriched air at about 1000° C. after mixing the oxygen gas with air. The heat of the oxygen-enriched air is recovered in the gas turbine 21 as a part of electric power generated by the gas turbine 21, and said oxygen-enriched air is also used as an oxidizing agent for the fuel. The electric power, generated by the gas turbine 21 and the steam turbine 30, is supplied to the high-temperature steam electrolyzer 20 for performing electrolysis. The gas turbine 21 emits hot exhaust gas (about 300° C.) which enters the feed water heater 33 for heat recovery.

As mentioned above, the high-temperature steam electrolyzer 20 generates the hydrogen gas 22. The hydrogen gas 22 enters the carbon dioxide heater 51, which is supplied with carbon dioxide gas 50 recovered from a carbon dioxide source such as thermoelectric power stations (not shown). After leaving the carbon dioxide heater 51, the hydrogen gas 22 further enters a rectifying column 58 thereby heating the column. Finally, the hydrogen gas is mixed with carbon dioxide discharged from the carbon dioxide heater 51, and the mixture is pressurized by the compressor 52 and is then fed to a reverse shift reactor 53.

The reverse shift reactor 53 reacts carbon dioxide with hydrogen to form carbon monoxide and steam. The reaction gas passes through the adsorptive high-temperature dryer 54 for the removal of steam. The removed steam enters the feed water heater 32 for heat recovery, and is finally mixed with the fresh water 44 discharged from the seawater desalination unit 40. The reaction gas which has been freed of steam is recycled to the reverse shift reactor 53 by a circulation compressor 55 so as to establish a desired gas composition. The thus obtained gas is fed to the methanol synthesis column 56. The methanol synthesis column 56 discharges methanol gas of low concentration, which is recycled by a circulation compressor 57 until a desired methanol concentration is reached. The methanol gas of a desired concentration is finally rectified by the rectifying column 58 which is heated with carbon dioxide gas heated by the heater 51. In this way there is obtained methanol 59.

In this embodiment, the nuclear heat of the HTGR 10 generates steam, which in turn generates electric power. The steam generated by the nuclear heat is converted into the hydrogen gas 22 by the high-temperature steam electrolyzer 20. And the hydrogen gas 22 is reacted with carbon monoxide converted from carbon dioxide from the carbon dioxide source, to yield methanol. Therefore, it may be said that the thus produced methanol has the nuclear energy in a converted form. Moreover, since the methanol is produced from carbon dioxide originating from the carbon dioxide source, it adds no carbon dioxide to the atmosphere after its combustion. Accordingly with this embodiment, it is possible to provide a method for producing methanol by the use of nuclear heat of HTGR, which can contribute to the reduction of carbon dioxide.

In addition, this embodiment employs for the production of methanol the reverse shift reactor 53 which yields a gas of almost the same composition as that used in the conventional methanol synthesis. Therefore, this embodiment can be carried out using a conventional methanol synthesis column 56.

Second Embodiment

Figure 3:
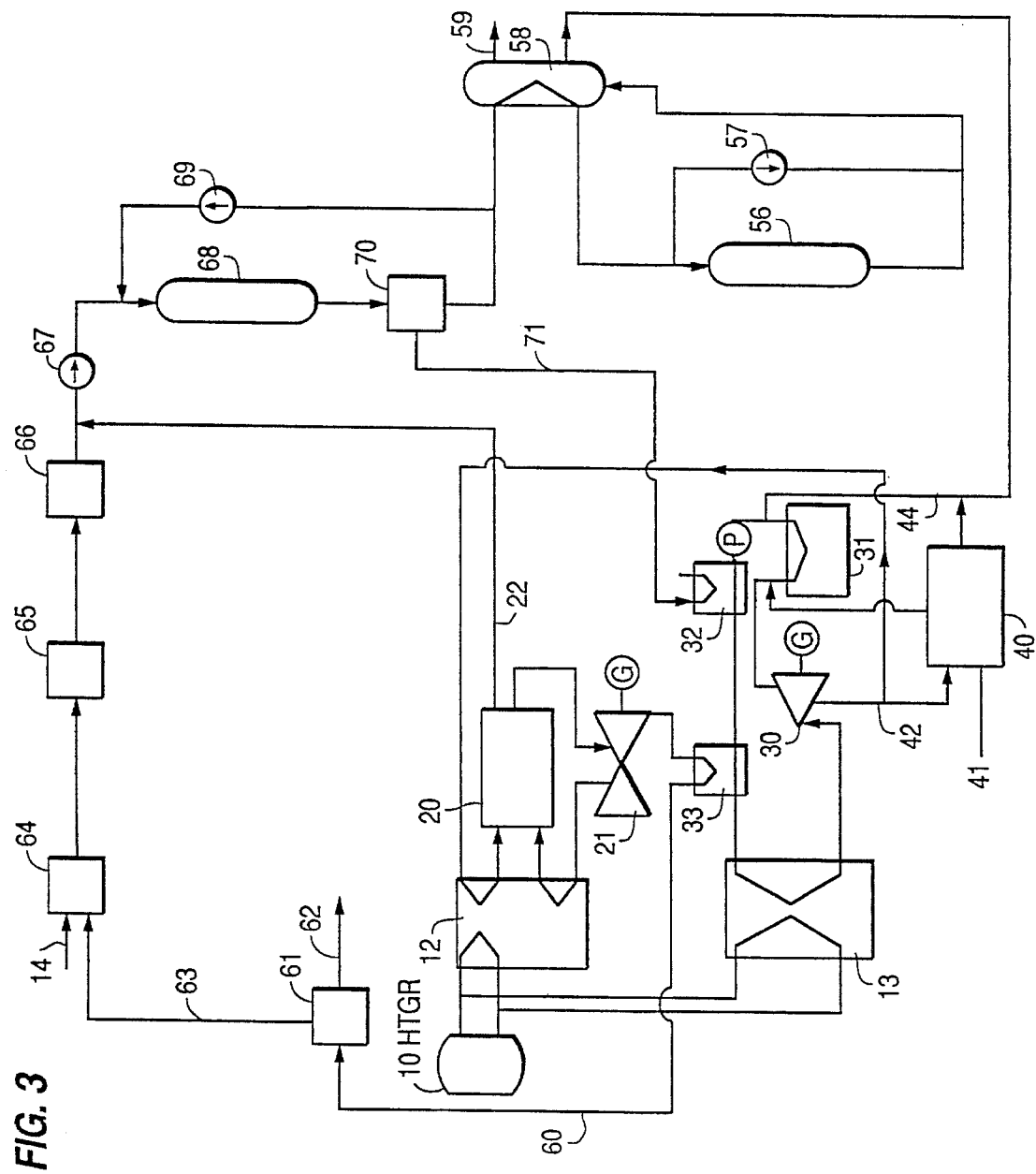
FIG. 3 is a schematic diagram of the second embodiment of the present invention.

The second embodiment of the present invention will be described with reference to FIG. 3. Referring to FIG. 3, there is shown the HTGR 10, which discharges high-temperature helium gas. The helium gas enters the intermediate heat exchanger 12 and steam generator 13 to supply them with heat. The steam generator 13 generates steam which enters the steam turbine 30 to drive it. The steam turbine 30 generates electric power necessary for the electrolysis to be carried out by the high-temperature steam electrolyzer explained below. The steam turbine 30 discharges steam which passes through the condenser 31 and the feed water heaters 32 and 33 and returns to the steam generator 13.

The steam turbine 30 has the low-pressure stage which permits steam (at 10 atm) to bleed. Part of the bleeding steam 42 enters the high-temperature steam electrolyzer 20 and the remainder enters the seawater desalination unit 40, which is supplied with seawater 41 and discharges fresh water 44. The fresh water 44 is fed to the power plant after mixing with the condensed water discharged from the condenser 31.

The high-temperature steam electrolyzer 20 is supplied with part of the bleeding steam 42 from the low-pressure stage of the steam turbine 30 after it has been heated to 700°–1000° C. by the intermediate heat exchanger 12 supplied with high-temperature helium gas from the HTGR 10. The high-temperature steam electrolyzer 20 is also supplied with air for heating and heat removal which is compressed to about 10 atm by the compressor coupled to the gas turbine 21 and heated to 700°–1000° C. by the intermediate heat exchanger 12.

The high-temperature steam electrolyzer 20 may be the same one as used in the first embodiment which is shown in FIG. 2.

As in the first embodiment, the high-temperature steam electrolyzer 20 decomposes steam into hydrogen gas and oxygen gas. It discharges the oxygen gas in the form of oxygen-enriched air at about 1000° C. after mixing the oxygen gas with air. The oxygen-enriched air enters the gas turbine 21 to function as an energy source. The gas turbine 21 also generates electric power which is combined with electric power generated by the steam turbine 30. The electric power is supplied to the high-temperature steam electrolyzer 20 for performing electrolysis. The gas turbine 21 emits hot exhaust gas (about 300° C.) which enters the feed water heater 33 for heat recovery.

After passing through the feed water heater 33 for heat recovery, the oxygen-enriched air 60 enters a nitrogen separator 61 (pressure-swing type absorber). The removed nitrogen 62 is discharged from the separator 61. The nitrogen-free oxygen gas 63 is fed to a coal gasification furnace 64 in which it is used as an oxidizing agent. The coal gasification furnace 64 converts the coal 14 fed to it into a gasified gas containing carbon monoxide, carbon dioxide, and hydrogen. This gas passes through a desulfurizer 65 and a dust remover 66 and is mixed with the hydrogen gas 22 generated by the high-temperature steam electrolyzer 20. The mixed gas is pressurized up to 50–100 atm by a compressor 67 and is then fed to a reverse shift reactor 68.

The reverse shift reactor 68 decomposes carbon dioxide and hydrogen into carbon monoxide and steam by facilitating a reverse shift reaction. The reaction gas passes through an adsorptive high-temperature dryer 70 for the removal of steam. The removed steam 71 enters the feed water heater 32 for heat recovery. The reaction gas discharged from the reverse shift reactor 68 is recycled to the reverse shift reactor 68 by a circulation compressor 69 so as to establish a desired gas composition. The thus obtained gas is fed to the methanol synthesis column 56 of a known type. The methanol synthesis column 56 discharges methanol gas of low concentration, which is recycled by the circulation compressor 57 until a desired methanol concentration is reached. The methanol gas of desired concentration is finally rectified by the rectifying column 58 which is heated with the reaction gas discharged from the high-temperature dryer 70. In this way there is obtained methanol 59.

In this embodiment, the steam turbine 30 and the gas turbine 21 generate the electric power using the nuclear heat of the HTGR 10. The nuclear heat also generates steam in the steam generator 13 and heats the steam in the intermediate heater 12, and the heated steam is converted into hydrogen by the high-temperature steam electrolyzer 20 using said electric power. Therefore, it may be said that the thus produced methanol has the nuclear energy in a converted form. Moreover, since the methanol is produced from the hydrogen and a coal-gasified gas containing carbon monoxide, carbon dioxide, and hydrogen, the produced methanol has the nuclear energy in a converted form.

Although the amount of carbon dioxide generated by burning the methanol produced by this embodiment is equal to that by burning the coal (raw material), the amount of heat generated by burning the methanol increases corresponding to the hydrogen added. Accordingly, the amount of carbon dioxide generated per calorific power can be reduced by using the methanol produced by this embodiment.

Third Embodiment

Figure 4:
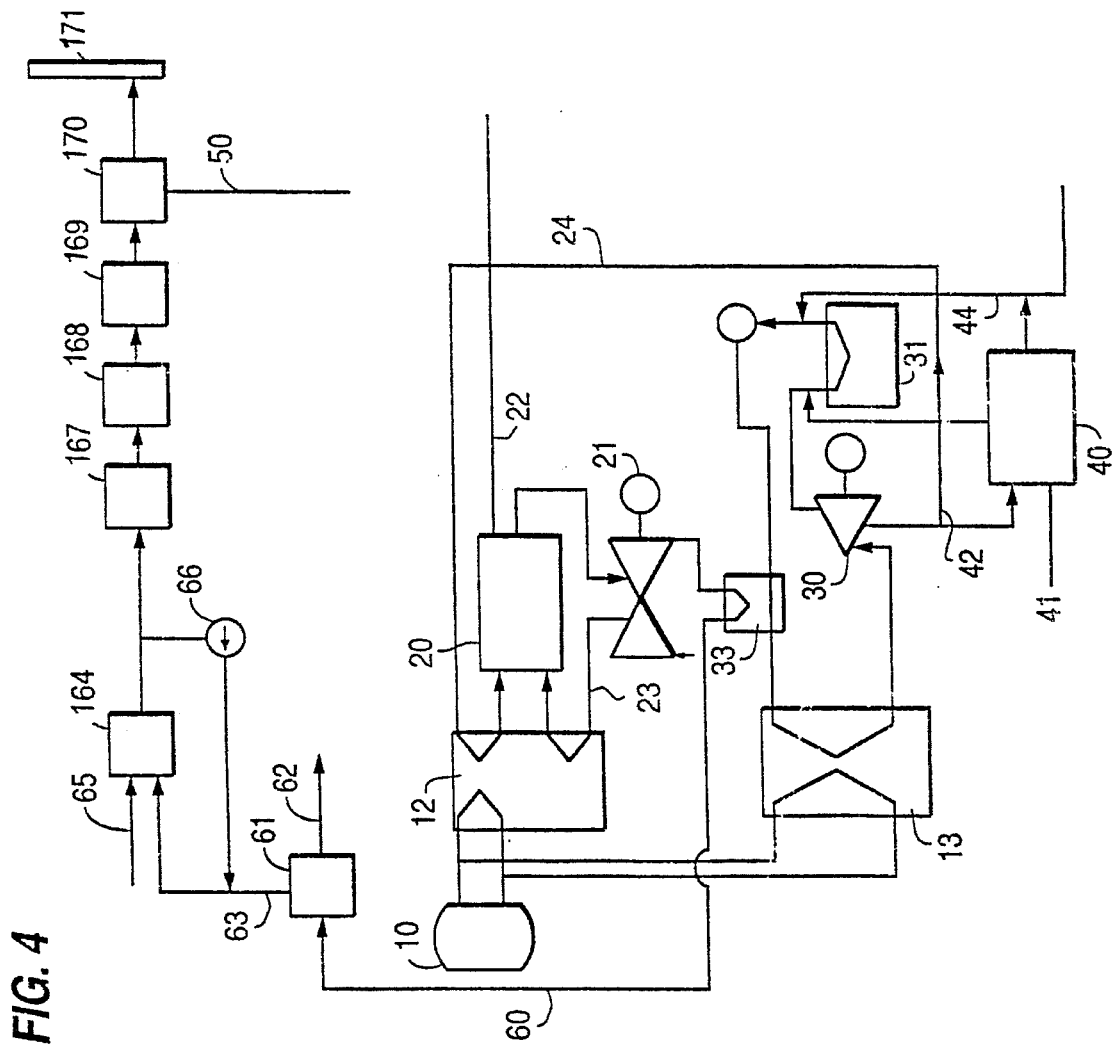
FIG. 4 is a schematic diagram of the third embodiment of the present invent ion.
Figure 5:
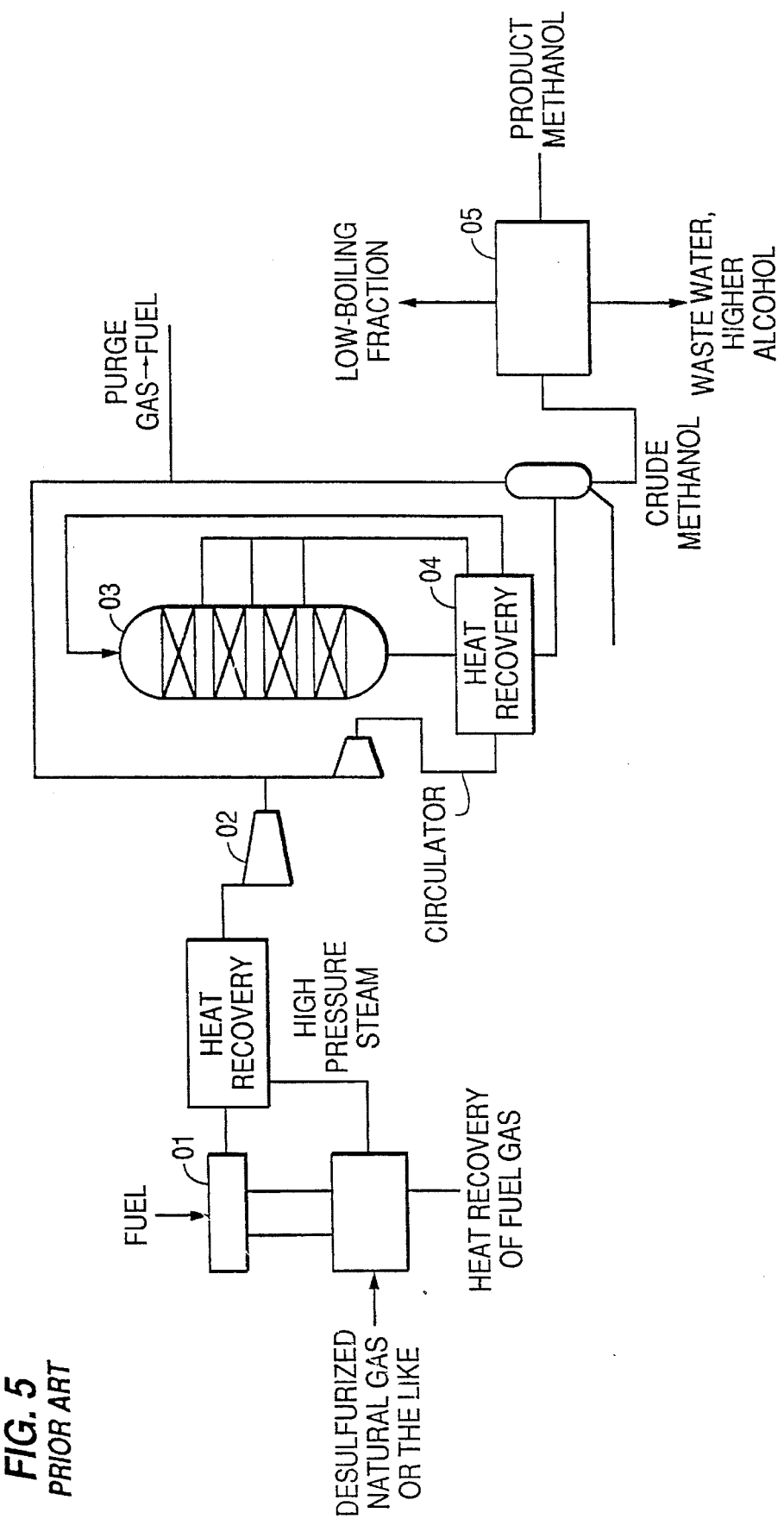
FIG. 5 is a schematic diagram illustrating the conventional process for methanol synthesis.

The third embodiment of the present invention will be described with reference to FIG. 4. In FIG. 4, HTGR 10, an intermediate heat exchanger 12, a steam generator 13, a high temperature steam electrolyzer 20, a gas turbine 21, a steam turbine 30, a condenser 31, feed water heaters 32, 33, a seawater desalination unit 40 and a nitrogen separator (pressure-swing type absorber) 61 are the same as those in the second embodiment shown in FIG. 3, and an explanation thereof will be abbreviated.

In this embodiment, the oxygen enriched air 60, passed through the feed water heater 33 for heat recovery, enters the nitrogen separator 61. Oxygen 63 generated in said nitrogen separator 61 by removing nitrogen 62 is supplied to a boiler 164 of a thermal power plant as combustion air. In the boiler 164, some of the exhaust gas is recirculated by an exhaust gas recirculation fan 166 and it is used as mixed with oxygen 63. The remainder of the exhaust gas passes through a denitrifier 167, a desulfurizer 168 and a dust remover 169 and it enters a $CO_2$ gas separator (pressure-swing type) 170. In the $CO_2$ gas separator 170, $CO_2$ in the exhaust gas is removed and then the exhaust gas is discharged into the air from a chimney 171.

Electric power generated by the gas turbine 21 and the steam turbine 30 is utilized for performing electrolysis in the high-temperature steam electrolyzer 20.

Further, oxygen gas 22 generated by the high-temperature steam electrolyzer 20 and $CO_2$ 50 separated in the $CO_2$ gas separator 170 can be used for synthesizing methanol as in the second embodiment.

As mentioned above, the present invention provides a process for producing methanol which employs the high-temperature steam electrolyzer containing a solid electrolyte which electrolyzes steam by using the high-temperature nuclear heat of an HTGR and the electric power generated by it. It may be said, therefore, that the electrolyzer converts the nuclear energy into hydrogen. The thus produced hydrogen is mixed with a gas composed of carbon monoxide, carbon dioxide, and hydrogen, and the mixed gas undergoes a reverse shift reaction to yield a gas of a desired composition for methanol synthesis. The thus produced methanol generates an additional amount of heat corresponding to the hydrogen resulting from the nuclear heat. Therefore, it gives rise to a less amount of carbon dioxide per calorific power. In other words, so to speak, it contains part of nuclear energy, and it contributes to the reduction of emitted carbon dioxide if it is used as an automotive fuel, etc.

Moreover, since the process of the present invention employs the reverse shift reaction for methanol synthesis, it is possible to obtain a feedstock gas of the same composition as the conventional one. This makes it possible to practice the present invention by using the existing methanol synthesis column, without a need for developing a new reaction catalyst.

Further, as mentioned above, in the power generating plant according to the present invention, because the oxygen-enriched air generated by the high-temperature steam electrolyzer is utilized as combustion air in the power generating plant, the following advantages can be obtained:

(1) The amount of nitrogen to be removed in the present invention is less than that of the prior art, because nitrogen is removed from the oxygen-enriched air with oxygen density higher than air in the present invention whereas nitrogen is removed from air using the nitrogen separator such as a pressure-swing type in the prior art. Accordingly, the present invention can reduce the power for removing nitrogen.

(2) By using the oxygen-enriched air in the present invention, the amount of the exhaust gas, which enters the devices of the power plant such as the denitrifier, the desulfurizer, the dust remover and the $CO_2$ separator, decreases and hence the volume of the plant and the cost of its construction can be reduced.

What is claimed is:

1. A power generating plant comprising:

a high-temperature gas-cooled nuclear reactor;

a steam electrolytic cell that converts steam into oxygen and hydrogen, said cell having a steam inlet, an oxygen outlet through which the oxygen produced by the cell passes from the cell, and a hydrogen outlet through which hydrogen produced by the cell passes from the cell;

an air compressor, and a first line placing an outlet of said air compressor in communication with the oxygen outlet of the steam electrolytic cell;

a source of water, and a second line placing said source of water in communication with the steam inlet of said steam electrolytic cell;

a steam generator in the form of a heat exchanger operatively connected to said reactor and to said second line such that heat generated by said reactor is transferred to water flowing through said second line toward said steam electrolyzer cell to produce steam; and a combustor connected to the oxygen outlet of said steam electrolytic cell such that oxygen-enriched air, constituted by air in communication with said oxygen outlet via said first line and oxygen produced by the cell, flows to said combustor.

2. A power generating plant as claimed in claim 1, wherein said steam electrolytic cell has an air inlet to which said first line is connected, and an internal chamber defined between said air inlet and said oxygen outlet, and further comprising an intermediate heat exchanger through which said first line passes and to which said second line passes after passing through said steam generator, said intermediate heat exchanger also being operatively connected to said reactor such that heat produced by said reactor heats the air flowing through said first line and the steam flowing through said second line.

3. A power generating plant as claimed in claim 1, wherein said source of water is a seawater desalination unit.

4. A power generating plant as claimed in claim 2, wherein said source of water is a seawater desalination unit.

5. A power generating plant as claimed in claim 1, wherein said combustor is part of a furnace.

6. A power generating plant as claimed in claim 2, wherein said combustor is part of a furnace.

7. A power generating plant as claimed in claim 1, wherein said combustor is part of a boiler.

8. A power generating plant as claimed in claim 2, wherein said combustor is part of a boiler.

9. A power generating plant as claimed in claim 1, and further comprising a steam turbine connected in-line with said second line downstream of said steam generator such that steam produced by said steam generator drives said steam turbine, and a generator operatively connected both to said steam turbine so as to be driven thereby and to said steam electrolytic cell so as to supply power to said cell.

10. A power generating plant as claimed in claim 2, and further comprising a steam turbine connected in-line with said second line downstream of said steam generator such that steam produced by said steam generator drives said steam turbine, and a generator operatively connected both to said steam turbine so as to be driven thereby and to said steam electrolytic cell so as to supply power to said cell.

\* \* \* \* \*

UNITED STATES PATENT AND TRADEMARK OFFICE
CERTIFICATE OF CORRECTION

PATENT NO. : 5,479,462
DATED : December 26, 1995
INVENTOR(S) : Yasihiro YAMAUCHI et al.

It is certified that error appears in the above-identified patent and that said Letters Patent is hereby corrected as shown below:

On the title page, item 75, the sixth inventor's first name is corrected to read --Kensuke--.

Signed and Sealed this

Thirtieth Day of April, 1996

Attest:

BRUCE LEHMAN

*Attesting Officer*     Commissioner of Patents and Trademarks